United States Patent [19]
Pellico et al.

[11] 4,269,822
[45] May 26, 1981

[54] ANTISEPTIC DENTIFRICE

[75] Inventors: Michael A. Pellico, Los Angeles; Robert E. Montgomery, West Los Angeles, both of Calif.

[73] Assignee: Laclede Professional Products, Inc., Brooklyn, N.Y.

[21] Appl. No.: 182,384

[22] Filed: Aug. 29, 1980

Related U.S. Application Data

[63] Continuation-in-part of Ser. No. 59,243, Jul. 20, 1979, abandoned.

[51] Int. Cl.³ .................. A61K 7/22; A61K 7/28; A61K 37/50; A61K 31/195
[52] U.S. Cl. .................. 424/50; 424/54; 424/94; 424/319
[58] Field of Search .................. 424/50, 54, 94, 319

[56] References Cited

U.S. PATENT DOCUMENTS

| | | | |
|---|---|---|---|
| 85,166 | 12/1868 | Colburn | 424/58 X |
| 111,821 | 2/1871 | Danforth | 424/58 |
| 2,124,971 | 7/1938 | Eisenberg et al. | 424/49 |
| 2,773,801 | 12/1956 | Fox | 424/49 |
| 2,891,868 | 6/1959 | Heggie et al. | 424/50 X |
| 3,574,824 | 4/1971 | Echeandia et al. | 424/50 |
| 3,703,578 | 11/1972 | Cella et al. | 424/49 |
| 3,934,000 | 1/1976 | Barth | 424/49 |
| 4,071,614 | 1/1978 | Grimm | 424/49 |
| 4,132,771 | 1/1979 | Schreiber et al. | 424/52 |
| 4,150,113 | 4/1979 | Hoogendoorn et al. | 424/50 |
| 4,159,316 | 6/1979 | Janoszewski et al. | 424/49 |

FOREIGN PATENT DOCUMENTS 4675M  1/1967  France .................. 424/50

*Primary Examiner*—Shep K. Rose
*Attorney, Agent, or Firm*—Donald Diamond

[57] ABSTRACT

An antiseptic dentifrice is provided which contains an enzyme system comprising an oxidizable amino acid substrate and an oxidoreductase enzyme specific to such substrate for producing hydrogen peroxide and ammonia upon oral application of the dentifrice. In an illustrative enzyme system for this purpose, the substrate is glycine and the oxidoreductase enzyme specific to this substrate is glycine oxidase.

8 Claims, No Drawings

ANTISEPTIC DENTIFRICE

CROSS-REFERENCE TO RELATED APPLICATION

This application is a continuation-in-part of U.S. Patent Application Ser. No. 059,243 filed July 20, 1979 now abandoned, for Antiseptic Dentifrice.

BACKGROUND OF THE INVENTION

This invention relates to dentifrice compositions and, more particularly, to antiseptic dentifrice compositions wherein hydrogen peroxide and ammonia are produced in situ during oral application of the dentifrice.

Dentifrices, in powder, paste, cream and liquid forms, are used for both cosmetic and therapeutic purposes. Consistent with these purposes, dentifrices are formulated to contain active ingredients such as cleansing and polishing materials, as well as various antibacterial and anticaries agents for use as aids in the prevention of tooth decay.

It is generally understood in the dental art that certain kinds of tooth decay are initiated by acid etching of the tooth enamel with the source of the acid being a metabolite resulting from bacterial and enzymatic action on food particles in the oral cavity. It is hypothesized that plaque—which is a soft accumulation on the tooth surfaces consisting of an organized structure of microorganisms, proteinaceous and carbohydrate substances, epithelial cells, and food debris—is a contributory factor in the development of various pathological conditions of the teeth and soft tissue of the oral cavity. It has been suggested that the saccharolytic organisms of the oral cavity, which are associates with the plaque, cause decalcification beneath the plaque matrix through metobolic activity which results in the accumulation and localized concentration of organic acids. The etching and decalcification of the enamel may continue until the pulp chamber of the tooth is reached.

A wide variety of materials have been considered for use as decay-preventative agents in dentifrice compositions. Some of the substances which have been so considered include para-aminobenzoic acid, a combination of urea and urease to produce ammonia during oral application of the dentifrice, chlorophyll, perflourinated long chain organic compounds, complex iodine, penicillin, benzohydroxamic acid, and glucose oxidase to produce hydrogen peroxide during oral application of the dentifrice.

U.S. Pat. No. 2,526,614 (Butterfield, 1950) discloses the incorporation into a dentifrice of an enzyme system comprising urea and urease which produces ammonia in the presence of moisture that is encountered during oral application of the dentifrice. The patentee reports that the action of the ammonia together with residual urea is bacterocidal to acidogenic organisms and antienzymatic to the production of lactic acid by such organisms. In addition, it is pointed out that the action of ammonia produced from this enzyme system dissolves mucin plaques.

U.S. Pat. No. 3,427,380 (Kirkland, 1969) discloses that oral organisms produce a capsular material which is a factor in holding plaque together and allowing its further growth and that the oral application of a dentifrice containing para-aminobenzoic acid inhibits capsule formation by such organisms and thereby retards the development of dental plaque without inhibiting the growth of these organisms.

U.S. Pat. No. 3,137,634 (Schiraldi, 1964) discloses that the oral application of a dentifrice composition containing, for example, potassium copper chlorophyllin, dicalcium phosphate dihydrate, and tetrasodium pyrophosphate is useful in the treatment of gum diseases such as periodontal disorders like gingivitis, pyorrhea and trench mouth and, in addition, reduces undesirable breath odors.

U.S. Pat. No. 3,227,618 (Dunellen, 1966) in the background portion of the specification, recites that it has been disclosed that treatment of tooth enamel with a mixture of stannous flouride, hydrogen peroxide and insoluble sodium metaphosphate increases the enamel hardness as described in *The Journal of the American Dental Association*, May, 1950, Vol. 40, pg. 513–519.

Merck Index, 9th Edition, 1976, at page 633, discloses that hydrogen peroxide solution 3% contains 2.5–3.5 wt. % of hydrogen peroxide which is equivalent to 8–12 volumes of oxygen, and that this solution is a topical anti-infective which is useful in pharmaceutical preparations such as mouthwashes, dentifrices, and sanitary lotions.

U.S. Pat. No. 4,150,133 (Hoogendorn et al, 1979) discloses an enzymatic dentifrice containing glucose oxidase which acts on glucose present in saliva and tooth plaque to produce hydrogen peroxide.

Hydrogen peroxide is a fast acting, broad spectrum oral antiseptic. Unlike other anitbacterials which continue into the digestive tract, hydrogen peroxide has the advantage of quickly breaking down into oxygen and water in the oral cavity. Hydrogen peroxide is also converted into oxygen and water in the oral cavity by the enzymatic action of catalase which is present in saliva.

Previous attempts to incorporate hydrogen peroxide into dentifrices such as toothpaste have met with limited success, due to the instability of hydrogen peroxide in the packaged product.

SUMMARY OF THE INVENTION

In accordance with this invention, there is provided an antiseptic dentifrice containing an enzyme system comprising from about 0.01 to about 0.5 wt.% of an oxidizable amino acid substrate and from about 50 IU to about 1,000 IU of an oxidoreductase enzyme specific to the substrate wherein the enzyme system is activated in the chemical environment of the oral cavity, upon oral application of the dentifrice, to produce hydrogen peroxide and ammonia.

DETAILED DESCRIPTION

The enzyme systems of this invention which can be incorporated into dentifrice compositions to produce hydrogen peroxide and ammonia during oral application of the dentifrice are illustrated by the substrate/enzyme combinations set forth in the following table:

| Oxidizable Substrate | Oxidoreductase Enzyme |
| --- | --- |
| (a) D-amino acids | D-amino acid oxidase |
| (b) L-amino acids | L-amino acid oxidase |
| (c) Glycine | glycine oxidase |

(a) D-amino acid oxidase catalyzes the interaction of D-amino acids such as the D isomers of proline, methionine, isoleucine, alanine, valine and phenylalanine together with water and oxygen to produce hydrogen peroxide, ammonia and the corresponding alpha-keto acids;

(b) L-amino acid oxidase catalyzes the interaction of L-amino acids such as the L isomers of isoleucine, alpha-amino butyric acid, citrulline, histidine, leucine, methionine, norleucine, norvaline, phenylalanine, tryptophane and tyrosine together with water and oxygen to produce hydrogen peroxide, ammonia and the corresponding alpha-keto acids; and (c) Glycine oxidase catalyzes the interaction of glycine, water and oxygen to produce hydrogen peroxide, ammonia and glyoxylic acid.

The characteristics of the enzymes from specific sources are as follows:

(a) D-Amino Acid Oxidase from Hog Kidney
  (i) Molecular Weight: 90,000 (Antonini et al., 1966).
  (ii) Composition: A glycoprotein containing two molecules of flavine-adenine dinucleotide.
  (iii) Optimum pH: 9.
  (iv) Inhibitors: certain heavy metals.

(b) L-Amino Acid Oxidase from Crotalus Adamanteus:
  (i) Molecular Weight: 140,000 (DeKok et al., 1969).
  (ii) Composition: a glycoprotein containing two molecules of flavine-adenine dinucleotide.
  (iii) Optimum pH: 7.5 (for leucine).
  (iv) Inhibitors: aromatic carboxylates.

(c) Glycine Oxidase
  (i) Molecular Weight: 90,000
  (ii) Composition: A glycoprotein containing two molecules of flavine-adenine dinucleotide
  (iii) Optimum pH: 8.6
  (iv) Inhibitors: Certain heavy metals.

The enzyme systems of this invention, comprising oxidizable amino acid substrate and oxidoreductase enzyme specific to such substrate, are advantageously incorporated into a dentifrice composition as, for example, toothpaste. Since water promotes the oxidation/reduction reactions of this invention and is also a reactant in those reactions, the use of water in formulating the dentifrice compositions should be at a relatively low concentration level in order to impart maximum stability and shelf life to the compositions. For this purpose, it has been found to be essential to limit any water present in the dentifrice to an amount not more than about 10 wt.%. In view of this water limitation, a non-aqueous fluid carrier is advantageously employed in the toothpaste formulation so as to provide the formulation with pressure responsive flow characteristics. Any suitable non-aqueous fluid may be used for this purpose. Organic fluid carriers, such as glycerine or propylene glycol provide a stable toothpaste environment for the enzyme systems of this invention. The non-aqueous fluid carrier is generally present in the dentifrice composition in an amount from about 30 to about 60 wt.% and, preferqbly, in an amount from about 45 to about 55 wt.%.

The oxidizable substrate is generally present in the dentifrice in an amount from about 0.01 to about 0.5 wt.% while the oxidoreductase enzyme specific to the substrate is generally present in the dentifrice in an amount from about 50 to about 1,000 International Units. An International Unit is that amount of enzyme that will effect catalysis of 1.0 micromole of substrate per minute at pH 7.0 and 25° C.

Where the products of the activated enzyme system include a weak organic acid, it is advantageous to formulate the dentifrice with a buffering agent to neutralize the organic acid. A suitable buffering agent is sodium bicarbonate which can be present in the dentifrice in an amount up to about 6 wt.% as, for example, in an amount from about 4 to about 6 wt.%.

Dentifrices, especially toothpaste, are preferred oral compositions for the purpose of this invention. Dentifrice compositions typically contain an abrasive polishing material and a surfactant as well as flavoring, sweetening and coloring agents. Toothpaste usually also contains humectants and thickeners.

Any abrasive polishing material which does not excessively abrade dentin and is compatible with the oxidoreductase enzymes described herein can be used in the compositions of this invention. These include, for example, calcium carbonate, calcium pyrophosphate, dicalcumium phosphate, zirconium oxide and aluminum oxide. The abrasive polishing material is usually present in toothpaste in an amount from about 20 to about 60 wt.%.

The surfactants which can be used are those which yield substantial levels of foam and which are otherwise acceptable for use in the oral cavity and compatible with the oxidoreductase enzymes. A suitable surfactant is sodium lauryl sulfate. However, a protein surfactant or dioctyl sodium sulfosuccintate surfactant is preferred because these surface active materials have been found to be more compatible with the oxidoreductase enzymes. The surfactants can be employed at concentration levels ranging from about 0.5 to about 5.0 wt.%.

The following examples further illustrate the compositions of this invention. The term "Maypon" used in the examples is the trademark of Stepan Chemical Company, Fieldsboro, N.J. for a potassium coco condensate of hydrolyzed animal protein having a molecular weight between 750 and 1,500 and supplied as an aqueous solution containing 34 go 40% solids. The term "Super-Pro" used in the examples is the trademark of Stepan Chemical Company for an aqueous solution of sorbitol and triethanolamine condensate of hydrolyzed animal protein having a molecular weight between 750 and 1,500 with the solution having a solids content from 62–70%. The term "DSS" used in the examples is the abbreviation for dioctyl sodium sulfosuccinate. Distilled water is employed in the examples.

EXAMPLE 1

An antiseptic toothpaste was prepared having the following formulation:

| Composition | weight, grams |
| --- | --- |
| Glycerine | 500 |
| Calcium pyrophosphate | 400 |
| Water | 25 |
| Sodium bicarbonate | 50 |
| Super-Pro | 20 |
| Glycine | 0.5g |
| Glycine oxidase | 5000 IU |
| Coloring agent | 5 |
| Flavoring agent | 5 |

The toothpaste was prepared by dissolving the glycine in the glycerine, with agitation, and then blending and mixing into this mixture the calcium pyrophosphate, sodium bicarbonate and coloring and flavoring agents until the resulting mixture was smooth. Super- Pro and glycine oxidase were then sequentially blended into the batch.

The resulting toothpaste was packaged into conventional toothpaste tubes. The filled tubes were heated in an oven at 140° F. for seven days. At the end of this heating cycle, the tubes were slit open and there was no evidence of bubble formation or pressure build-up which indicated that the glycine/glycine oxidase enzyme system is stable in the toothpaste composition. The pH of the toothpaste varied from 6.8 to 6.9. An aliquot part of the heated toothpaste, which was cooled to ambient temperature, was added to a beaker of water with stirring and it was noted that the pH of the dispersion increased to 8.2 to 8.5 indicating the formation of ammonia and, in accordance with the reaction scheme, also indicated the formation of hydrogen peroxide.

EXAMPLE 2

The following examples show antiseptic toothpaste formulations incorporating various enzyme systems which produce ammonia and hydrogen peroxide during oral application of the toothpaste. These examples also show the varying concentration levels for the ingredients of the enzyme systems and, in addition, show examples of a fluid carrier, cleaning and polishing agent and surfactants which are compatible with these enzyme systems.

| 2A | |
|---|---|
| Composition | weight, grams |
| Glycerine | 50.0 |
| Calcium pyrophosphate | 40.2 |
| Sodium bicarbonate | 5.0 |
| Maypon | 2.0 |
| D-alanine | 0.3 |
| D-amino acid oxidase | 500 IU |

| 2B | |
|---|---|
| Composition | weight, grams |
| Glycerine | 50.0 |
| Water | 1.0 |
| Calcium pyrophosphate | 41.6 |
| Sodium bicarbonate | 5.0 |
| Super-Pro | 2.0 |
| L-phenylalanine | 0.4 |
| L-amino acid oxidase | 400 IU |

| 2C | |
|---|---|
| Composition | weight, grams |
| Glycerine | 50.0 |
| Water | 2.5 |
| Dicalcium phosphate | 41.0 |
| Sodium bicarbonate | 5.0 |
| Maypon | 1.0 |
| L-leucine | 0.5g |
| L-amino acid oxidase | 500 IU |

| 2D | |
|---|---|
| Composition | weight, grams |
| Glycerine | 45.0 |
| Water | 5.0 |
| Calcium pyrophosphate | 42.5 |
| Sodium bicarbonate | 5.0 |
| DSS | 2.0 |
| L-tyrosine | 0.5 |
| L-amino acid oxidase | 900 IU |

| 2E | |
|---|---|
| Composition | weight, grams |
| Glycerine | 50.0 |
| Water | 1.0 |
| Dicalcium phosphate | 41.7 |
| Sodium bicarbonate | 5.0 |
| DSS | 2.0 |
| D-proline | 0.3 |
| D-amino acid oxidase | 100 IU |

| 2F | |
|---|---|
| Composition | weight, grams |
| Glycerine | 50.0 |
| Water | 7.5 |
| Calcium pyrophosphate | 41.1 |
| Sodium bicarbonate | 5.0 |
| Super-Pro | 2.0 |
| D-alanine | 0.4 |
| D-amino acid oxidase | 600 IU |

| 2G | |
|---|---|
| Composition | weight, grams |
| Glycerine | 40.0 |
| Water | 5.0 |
| Dicalcium phosphate | 28.8 |
| Zirconium oxide | 20.0 |
| Sodium bicarbonate | 5.0 |
| Super-Pro | 1.0 |
| D-methionine | 0.2 |
| D-amino acid oxidase | 200 IU |

In view of the foregoing description and examples, it will become apparent to those of ordinary skill in the art that equivalent modifications thereof may be made without departing from the spirit and scope of this invention.

That which is claimed is:

1. An antiseptic dentifrice containing from about 0.01 to about 0.5 wt.% of an oxidizable amino acid substrate and from about 50 to about 1,000 International Units of an oxidoreductase enzyme specific to said substrate for producing ammonia and hydrogen peroxide upon oral applicaton of said dentifrice, said dentifrice being stabilized against the production of ammonia and hydrogen peroxide prior to the oral application thereof by incorporating into the dentifrice a non-aqueous fluid carrier in an amount from about 30 to about 60 wt.% and limiting any water present in the dentifrice to an amount not more than about 10 wt.%.

2. The dentifrice of claim 1 wherein the substrate is a D-amino acid selected from the group consisting of D isomers of proline, methionine, isoleucine, alanine, valine and phenylalanine and the enzyme is D-amino acid oxidase.

3. The dentifrice of claim 1 wherein the substrate is a L-amino acid selected from the group consisting of L isomers of isoleucine, 2-aminobutanoic acid, citrulline, histidine, leucine, methionine, norleucine, norvaline, phenylalanine, tryptophane, and tyrosine and the enzyme is L-amino acid oxidase.

4. The dentifrice of claim 1 wherein the substrate is glycine and the enzyme is glycine oxidase.

5. The dentifrice of claim 1 wherein the non-aqueous fluid carrier is glycerin.

6. The dentifrice of claim 1 wherein the non-aqueous fluid carrier is propylene glycol.

7. The dentifrice of claim 1 which includes a protein surfactant in an amount from about 0.5 to about 5.0 wt.%.

8. The dentifrice of claim 1 which includes a dioctyl sodium sulfosuccinate surfactant in an amount from about 0.5 to about 5.0 wt.%.

* * * * *